United States Patent [19]

Jouquey et al.

[11] Patent Number: 4,639,336
[45] Date of Patent: Jan. 27, 1987

[54] NOVEL RADIOACTIVE ESTRADIENES LABELLED WITH IODINE

[75] Inventors: Alain Jouquey; Jean Salmon; Michel Mouren; Gaëtan Touyer, all of Paris, France

[73] Assignee: Roussel Uclaf, Paris, France

[21] Appl. No.: 620,455

[22] Filed: Jun. 14, 1984

[30] Foreign Application Priority Data

Jun. 14, 1983 [FR] France ............... 83 09812
Jun. 20, 1983 [FR] France ............... 83 10142

[51] Int. Cl.⁴ ............................................. C07J 1/00
[52] U.S. Cl. ........................... 260/397.5; 424/1.1; 514/182
[58] Field of Search ......... 260/397.45, 397.5; 514/182; 424/1.1

[56] References Cited
PUBLICATIONS

"Steroids"-vol. 32, No. 4 (1978), pp. 467–486, an article by Allen et al.

*Primary Examiner*—Elbert L. Roberts
*Attorney, Agent, or Firm*—Bierman and Muserlian

[57] ABSTRACT

Novel radioactive estradienes labelled with iodine of the formula

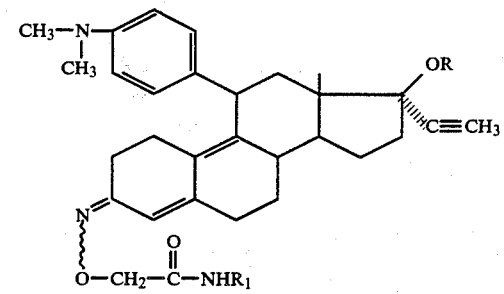

in the form of their syn or anti isomers or mixtures thereof wherein the wavy line indicates anti or syn position, R is selected from the group consisting of hydrogen, alkyl of 1 to 6 carbon atoms and acyl of an organic carboxylic acid of 1 to 12 carbon atoms and $R_1$ is the residue of an amino acid $R_1NH_2$ possessing an iodine acceptor group or a derivative thereof labelled with iodine $^{125}$ or $^{131}$ and their preparation and novel intermediates, antigens prepared from the compounds of formula I and bovine seric albumin or human seric albumin and their preparation and their use for the preparation of antibodies.

15 Claims, No Drawings

NOVEL RADIOACTIVE ESTRADIENES LABELLED WITH IODINE

STATE OF THE ART

U.S. Pat. No. 4,396,085 describes the starting compound of formula II and U.S. Pat. No. 4,069,305 describes radio immunological doses of different steroids. U.S. Pat. No. 4,358,435 describes radioactive and non-radioactive histamine derivatives of different steroids.

OBJECTS OF THE INVENTION

It is an object of the invention to provide the novel compounds of formula I, a process for their preparation and novel intermediates.

It is a further object of the invention to provide novel antigens and a process for their preparation.

It is an additional object of the invention to provide a process for the preparation of antibodies.

These and other objects and advantages of the invention will become obvious from the following detailed description.

THE INVENTION

The novel compounds of the invention are radioactive estradienes labelled with iodine of the formula

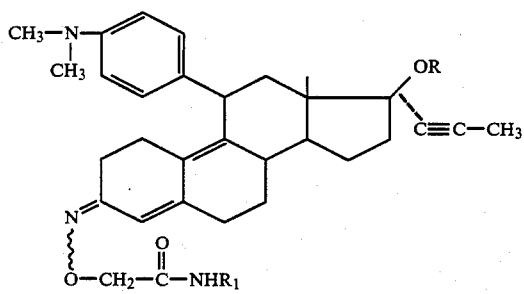

in the form of their syn or anti isomers or mixtures thereof wherein the wavy line indicates anti or syn position, R is selected from the group consisting of hydrogen, alkyl of 1 to 6 carbon atoms and acyl of an organic carboxylic acid of 1 to 12 carbon atoms and $R_1$ is the residue of an an amino acid $R_1NH_2$ possessing an iodure acceptor group or a derivative thereof labelled with iodine $^{125}$ or $^{131}$.

Examples of R are hydrogen; alkyl of 1 to 6 carbon atoms such as methyl, ethyl, propyl, isopropyl, butyl, sec-butyl, tert-butyl, pentyl, iso-pentyl, sec-pentyl, tert-pentyl, hexyl, iso-hexyl, sec-hexyl and tert-hexyl and acyl such as formyl, acetyl, propionyl, butyryl, isobutyryl, valeryl, hexanoyl, benzoyl, caprylyl, methoxy-carbonyl and or ethoxycarbonyl.

The residue of an amino acid derivative is preferably the residue of a decarboxylated derivative of an amino acid or a lower alkyl ester thereof. Among the preferred amino acids are histidine, tyrosine, histamine, tyramine and methyl tyrosinate, labelled with iodine 125 or 131.

Among the preferred compounds of formula I are the syn and anti isomers and mixtures thereof of 3-carboxymethyloxime of 11β-(4-dimethylaminophenyl)-17α-(prop-1-ynyl)-Δ$^{4,9}$-estradiene-17β-ol-3-one coupled to $^{125}$I histamine [product A] with the formula

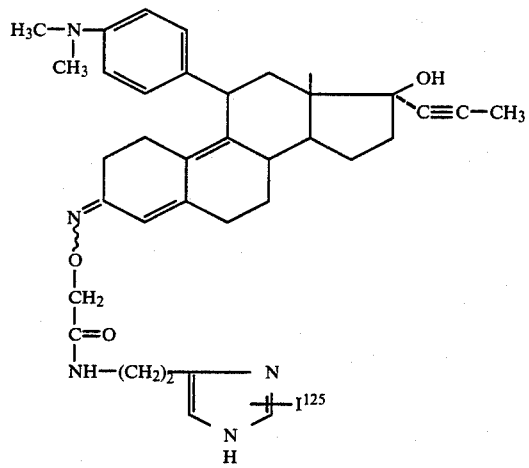

the iodine being able to be in the 2- or 5-position. The process of the invention for the preparation of products of formula I comprising reacting a product of the formula

II

H₃C—N(CH₃)—[structure]—OR
C≡C—CH₃ wherein R has the above definition with a carboxymethoxylamine halide in the presence of a base to obtain a compound of the formula

III

H₃C—N(CH₃)—[structure]—OR
C≡C—CH₃
N—O—CH₂
H—O—CO wherein the wavy line on the nitrogen indicates that the product is in the form of a mixture of syn and anti isomers, then fixing on the acid function of the product an activator group of the carbonyl function to obtain a compound of the formula

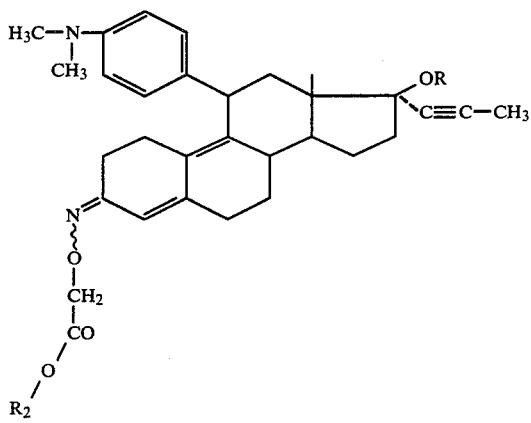

wherein R₂ is an activator group of the carbonyl function and the wavy line on the nitrogen indicates that this product is in the form of a mixture of syn and anti isomers and reacting the latter with an amino acid $R_1NH_2$ possessing an iodine acceptor group labelled with iodine[125] or [131] or with a derivative thereof to obtain the corresponding compound of formula I, which is isolated in the form of a mixture of syn and anti isomers, or which is separated, if desired, into its isomers, then, if necessary the 17-hydroxy function is etherified or esterified.

In a preferred mode of the process the amino acid iodine acceptor or the derivative of the amino acid is selected from the group consisting of histidine, tyrosine, histamine, tyramine and methyl tyrosinate; the carboxymethoxylamine halide is carboxymethoxylamine hemihydrochloride and the reaction is carried out under an inert atmosphere in the presence of sodium hydroxide; an activator group of the carbonyl function is fixed on the acid function by reaction with an alkyl haloformate in the presence of a tertiary base in an anhydrous medium and under an inert atmosphere.

In a very preferential mode of the process, the alkyl haloformate is isobutyl chloroformate and the operation is carried out in the presence of tri-n-butylamine: the amino acid reacted with the product of formula IV in which R₂ is an activator group of the carbonyl function is histamine labelled with iodine[125] or [131], and the operation is carried out under an inert atmosphere. The activation of the carbonyl function of the product of formula III can also be realized by reaction with N-hydroxy succinimide or dicyclohexylcarbodiimide, generators of activator groups of the said carbonyl function.

The etherification or the esterification of the 17-hydroxyl of the product of formula I wherein R is hydrogen can be effected according to usual methods. The etherification, for example, can be effected with an etherification agent such as an alkyl or aryl halide, or a dialkyl sulfate. The esterification, for example, can be effected with an esterification agent such as a functional derivative of an acid, such as an acid chloride or an anhydride.

To obtain the individual syn and anti isomers of the product of formula I, a product of formula III in the form of a mixture of syn and anti isomers wherein R has the above significance, is reacted with an esterification agent to esterify the carboxyl function, the syn isomer is separated from the anti isomer of the resulting ester and then the said ester function of each of the syn and anti isomers is separately saponified. The syn isomer and the anti isomer obtained are traited separately in order to fix an activator group of the carbonyl function on the liberated acid function, to obtain the corresponding mixed anhydrides which are reacted with an iodine acceptor amino acid labelled with iodine[125] or [131], or with a derivative of this acid to obtain the corresponding products of formula I in the form of the individual syn and anti isomers.

The products of formula I and particularly the 3-carboxymethyloxime of 11β-(4-dimethylaminophenyl)-17α-(prop-1-ynyl)-Δ⁴,⁹-estradiene-17β-ol-3-one in the form of a mixture of syn and anti isomers or in the form of the syn isomer and the anti isomer are coupled with $^{125}$I histamine (Product A) and it is useful for the the study and the radio-immunological determination of non-radioactive 11β-(4-dimethylaminophenyl)-17α-(prop-1-ynyl)-Δ⁴,⁹-estradiene-17β-ol-3-one (product B) and of its metabolites in biological fluids in man or in animals.

The novel intermediates of the invention are the products of formulae III and IV in the form of a mixture of syn and anti isomers or in the form of the syn or the anti isomer:

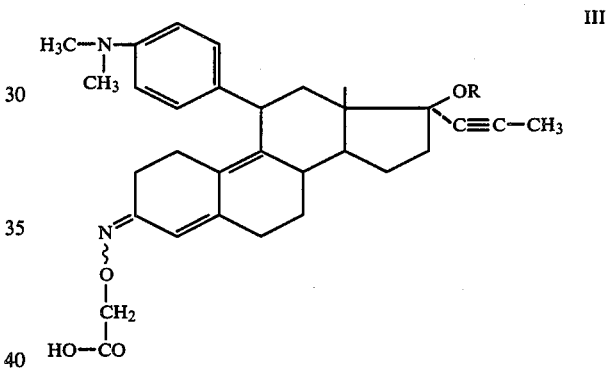

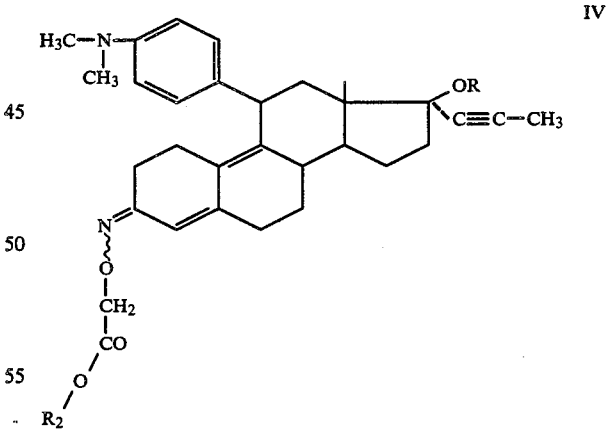

wherein the wavy line on the oximine nitrogen signifies that the oxime function can be in the syn or the anti position and R is hydrogen, alkyl of 1 to 6 carbon atoms or an acyl group of a carboxylic acid of 1 to 12 carbon atoms and R₂ is an activator group of the carbonyl function. Specific compounds are 3-carboxymethyloxime of 11β-(4-dimethylaminophenyl)-17α-(prop-1-ynyl)-Δ⁴,⁹-estradiene-17β-ol-3-one in the form of a mixture of syn and anti isomers or in the form of the syn isomer and the anti isomer, the mixed anhydride of 3-carboxymethyloxime of 11β-(4-dimethylaminophenyl)-17α-(prop-1-ynyl)-Δ$^{4,9}$-estradiene-17β-ol-3-one with isobutyl formate in the form of a mixture of syn and anti isomers or in the form of the syn isomer and the anti isomer:

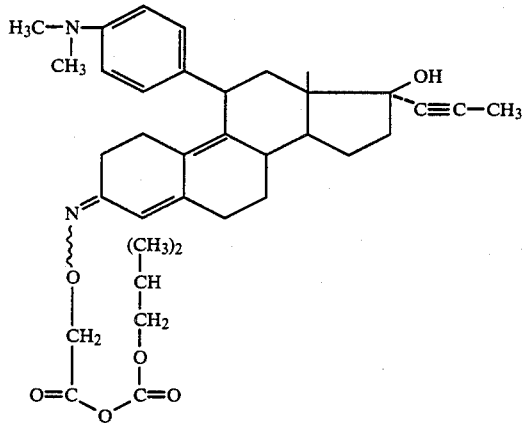

The products of formula III are useful starting products for the preparation of antigens which are also necessary for the radio-immunological determinations of the previously mentioned product B and its metabolites. Their use is characterized in that one of these products is combined with bovine seric albumin (BSA) or with human seric albumin (HSA) to obtain the desired antigen. Preferably a product of formula III in the form of a mixture of syn and anti isomers or in the form of the syn or the anti isomer is reacted with an alkyl halogenoformate in the presence of a tertiary base in an anhydrous medium and under an inert atmosphere for activation of the carbonyl function to obtain the corresponding mixed anhydride of the formula IV:

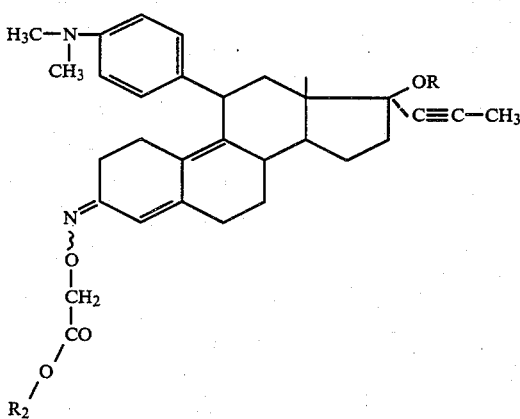

wherein R has the above definition and $R_2$ is —CO—O—alk, alk being alkyl of 1 to 6 carbon atoms which is combined with bovine seric albumin (BSA) or human seric albumin (HSA) to obtain the antigen.

In a preferred mode of the said process, the alkyl halo-formate is isobutyl chloroformate and the operation is carried out in the presence of tri-n-butylamine under an inert atmosphere and the mixed anhydride of formuma IV is reacted with the bovine seric albumin (BSA) or the human seric albumin (HSA) after having previously dissolved these latter in a water-dioxane mixture under an inert atmosphere.

The antigens of the invention are the anti-isomer or syn-isomer or mixtures thereof of the carboxymethyloxime of 11β-(4-dimethylaminophenyl)-17α-(prop-1-ynyl)-17β-OR-Δ$^{4,9}$-estradiene-3-one of the formulae

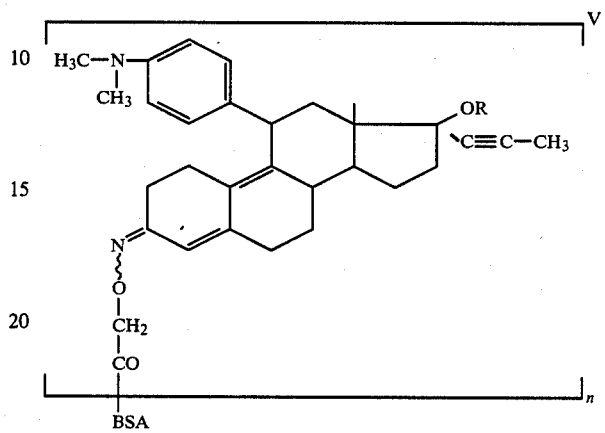

wherein n is 20 to 30 and the oxime part of the steroid is in the form of a mixture of syn and anti isomers or in the form of the syn or the anti isomer, and:

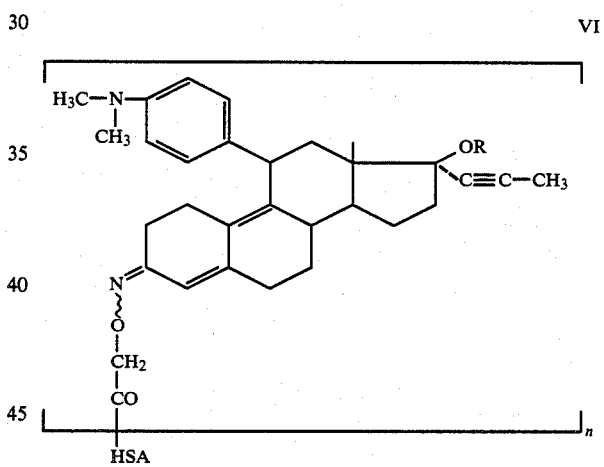

wherein n is 20 to 30 and the oxime part of the steroid is in the form of a mixture of syn and anti isomers, or in the form of the syn or the anti isomer.

The novel antigens of the invention are useful for the preparation of antibodies. The products of formula I and especially the 3-carboxy-methyloxime of 11β-(4-dimethylaminophenyl)-17α-(prop-1-ynyl)-Δ$^{4,9}$-estradiene-17β-ol-3-one coupled to ($^{125}$I) histamine [product A] in the form of a mixture of syn and anti isomers or in the form of the syn or the anti isomer, are used for the study and the radio-immunological determination of non-radioactive 11β-(4-dimethylaminophenyl)-17α-(prop-1-ynyl)-Δ$^{4,9}$-estradiene-17β-ol-3-one [product B] and its metabolitess in the biological fluids of man or animals. Product A, after its administration, can be followed in its evolution and in its behaviour in the biological fluids of man and animals.

In these studies, product A enables in particular an easy specific determination of quantities on the order of some tens of picograms per mil of biological fluid without having recourse to isolation and purification methods by chromatography before proceeding to the determination itself.

To study and determine by radio-immunological methods non-radioactive 11β-(4-dimethylaminophenyl)-17α-(prop-1-ynyl)-Δ$^{4,9}$-estradiene-17β-ol-3-one [product B], starting with this latter, antigens are prepared with bovine seric albumin (BSA) or with human seric albumin (HSA). The resulting antigens of formulae V and VI, can be used for the development of antibodies when they are injected into an animal in the presence of an adjuvant to obtain serums containing anti-bodies. These anti-bodies then serve as receptors of radio-active products and/or of non-radioactive products or as receptors of products of formula I and especially the 3-carboxymethyloxime of 11β-(4-dimethylaminophenyl)-17α-(prop-1-ynyl)-Δ$^{4,9}$ estradiene-17β-ol-3-one in the form of a mixture of syn and anti isomers or in the form of the syn isomer or the anti isomer coupled to ($^{125}$I) histamine [product A], as well as of non-radioactive 11β-(4-dimethylaminophenyl)-17α-(prop-1-ynyl)-Δ$^{4,9}$-estradiene-17β-ol-3-one [product B] and its metalbolites.

The presence of these anti-bodies is revealed with a product of formula I, and particularly with the 3-carboxymethyloxime of 11β-(4-dimethylaminophenyl)-17α-(prop-1-ynyl)-Δ$^{4,9}$-estradiene-17β-ol-3-one in the form of a mixture of syn and anti isomers or in the form of the syn isomer or the anti isomer coupled with the radio-active ($^{125}$I) histamine [product A]. One then proceeds to the determination of the product B or of its metabolites by conventional radio-immunological methods such as those described by: BERGSON et al, HORMONE Vol. 4 p. 557 (1964), and ABRAHAM, J. of CHEM. ENDOCRINAL METAB., Vol. 29 p. 866 (1969).

In the following examples there are described several preferred embodiments to illustrate the invention. However, it should be understood that the invention is not intended to be limited to the specific embodiments.

EXAMPLE 1

3-carboxymethyloxime of 11β-(4-dimethylaminophenyl)-17α-(prop-1-ynyl)-Δ$^{4,9}$-estradiene-17β-ol-3-one coupled with ($^{125}$I) histamine STEP A: 3-carboxymethyloxime of 11β-(4-dimethylaminophenyl)-17α-(prop-1-ynyl)-Δ$^{4,9}$-estradiene-17β-ol-3-one 665 mg of carboxymethoxylamine hemihydrochloride were added to a solution of 1 g of 11β-(4-dimethylaminophenyl)-17α-(prop-1-ynyl)-Δ$^{4,9}$-estradiene-17β-ol-3-one in 35 ml of ethanol and the mixture was stirred for about one hour at ambient temperature. 1.6 ml of N sodium hydroxide were added thereto and it was then concentrated to dryness under vacuum and the residue was taken up in chloroform and the solution was filtered. The filtrate was evaporated to dryness, the residue was chromatographed over silica gel. Elution with 7–3 chloroform/methanol was effected and the product was isolated, and triturated with isopropyl ether. The product was separated and dried under vacuum to obtain 1.13 g of 3-carboxymethyloxime of 11β-(4-dimethylaminophenyl)-17α-(prop-1-ynyl)-Δ$^{4,9}$-estradiene-17β-ol-3-one in the form of a mixture of its syn and anti isomers. Thin layer chromatography on silica gel and elution with an 8:2 chloroform/methanol mixture gave a product with an Rf=0.45.

STEP B: 3-carboxymethyloxime of 11β-(4-dimethylaminophenyl)-17α-(prop-1-ynyl)-Δ$^{4,9}$-estradiene-17β-ol-3-one coupled with ($^{125}$I) histamine in the form of a mixture of syn and anti isomers The mixed anhydride of 3-carboxymethyloxime of 11β-(4-dimethylaminophenyl)-17α-(prop-1-ynyl)-Δ$^{4,9}$-estradiene-17β-ol-3-one in the form of a mixture of syn and anti isomers with isobutyl formate was prepared by dissolving with stirring and under an inert atmosphere 3.5 mg of 3-carboxymethyloxime of the product of Step A in 50 μl of dioxane and 10 μl of a mixture of tri-n-butylamine and tetrahydrofuran (1:5) were added thereto. Then, 10 μl of a mixture of isobutyl chloroformate and tetrahydrofuran (1:10) were added and the mixture was stirred for half-an-hour at about 4° C. 3.4 ml of tetrahydrofuran were added, and a solution of the said mixed anhydrides was formed which was utilized as is for the following stage of the synthesis.

Iodation of the histamine

To 10 μl of a 2 mM solution of histamine in a 0.5M solution of sodium phosphate buffered to pH 8, there were successively added 1 mCi of sodium iodide$^{125}$ and 50 μg of chloramine T in 10 μl of distilled water. The mixture was stirred for about 90 seconds and then 300 μg of sodium metabisulfite dissolved in 10 μl of distilled water were added to obtain an aqueous solution of the desired product which was utilized as is for the following step of the synthesis. (Thin layer chromatography on silica with a methanol/triethylamine (98:2) solvent system gave Rf=0.1).

Condensation

50 μl of the previously prepared solution of mixed anhydrides were added under inert atmosphere to the iodated histamine solution obtained above with stirring and the mixture was allowed to stand for about one and half hours at about 4° C. under an inert atmosphere. The mixture was then diluted with 400 μl of 0.1M solution of sodium bicarbonate, and was extracted with 1.6 ml of methylene chloride. The organic phase was separated and evaporated to dryness under inert atmosphere. The residue was taken up in 250 μl of ethyl acetate, and the product was purified by high performance liquid chromatography, eluting with a 98.5:1.5 chloroform/methanol system. The solution, corresponding to two roughly separated peaks, was isolated and evaporated to dryness under an inert atmosphere. The residue were taken up in methanol to obtain a radio-active concentration in the product with an activity of 25 μCi/ml. In all, about 100 μCi/ml the product was done under inactinic light. Thin layer chromatography on silica and elution with a cyclohexane/ethanol/triethylamine (70:30:1) system gave an Rf=0.28.

EXAMPLE 2

Antigen starting with 3-carboxymethyloxime of 11β-(4-dimethylaminophenyl)-17α-(prop-1-ynyl)-Δ$^{4,9}$-estradiene-17β-ol-3-one in the form of a mixture of its syn and anti isomers and bovine seric albumin (BSA)

STEP A: Mixed anhydride of 3-carboxymethyloximine of 11β-(4-dimethylaminophenyl)-17α-(prop-1-ynyl)-Δ$^{4,9}$-estradiene-17β-ol-3-one in the form of a mixture of syn and anti isomers with isobutyl formate Under agitation and under an inert atmosphere, 63 mg of 3-carboxymethyloxime of 11β-(4-dimethylaminophenyl)-17α-(prop-1-ynyl)-Δ$^{4,9}$-estradiene-17β-ol-3-one one prepared in Step A of Example 1 were dissolved in 1.2 ml of dioxane and 57.5 μl of tri-n-butylamine were added thereto. Then the temperature was lowered to 13° C. and 16 μl of isobutyl chloroformate were added. The mixture was stirred at a temperature of about 13° C. for half-an-hour to obtain a solution of mixed anhydride of 3-carboxymethyloxime of 11β-(4-dimethylaminophenyl)-17α-(prop-1-ynyl)-Δ$^{4,9}$-estradiene-17β-ol-3-one in the form of a mixture of syn and anti isomers with isobutyl formate.

STEP B: Dissolving the bovine seric albumin

At 4° C. and with stirring under an inert atmosphere, 175 mg of bovine seric albumin were introduced into 0.5 ml of water, and after stirring for about 20 minutes when it was dissolved, 3 ml of dioxane and 170 μl of N sodium hydroxide were added successively.

STEP C: Combination

The mixed anhydride solution obtained in Step A was poured slowly into the bovine seric albumin solution obtained in Step B and the pH was adjusted to 8.9 by addition of N hydrochloric acid. The mixture was stirred for 5 hours at about 10° C. and the organic phase was then separated from the precipitate formed. The filtrate was diluted with 30 ml of distilled water and the pH was adjusted to 4.1 by adding N hydrochloric acid. The precipitate formed was separated and was taken up in 25 ml of a 1% aqueous solution of sodium bicarbonate. The resulting solution was left to stand and was then submitted to ultra-filtration. The solution was exhausted of molecules with a molecular weight <10-15000 by 510 ml of distilled water and then the final volume was adjusted to 17 ml. This solution was lyophilized over about 30 hours to obtain 169 mg of the antigen sought obtained.

| Analysis: | UV Spectrum |
|---|---|
| in water | :max. at 265 nm $E_1^1$ = 53 |
|  | :max. at 290 nm $E_1^1$ = 62 |
| in 0.1 N HCl | :max. at 290 nm $E_1^1$ = 61. |

| | Circular dichroism |
|---|---|
| in water: | max. at 222 nm $\Delta E_1^1$ = −0.305 |
|  | max. at 260 nm $\Delta E_1^1$ = −0.070 |
|  | max. at 289 nm $\Delta E_1^1$ = −0.050 |
| in 0.1 N HCl | max. at 222 nm $\Delta E_1^1$ = −0.250 |
|  | max. at 290 nm $\Delta E_1^1$ = +0.027 |

The product contained from 20 to 22 bound steroid groups per mole of protein.

EXAMPLE 3

Antigen starting with 3-carboxymethyloxime of 11β-(4-dimethylaminophenyl)-17α-(prop-1-ynyl)-Δ$^{4,9}$-estradiene-17β-ol-3-one in the form of a mixture of syn and anti isomers and human seric albumin (HSA)

Using the procedure of Step C of Example 2, but starting with the mixed anhydride solution of Step A and with a solution of human seric albumin prepared according to the method described in Step B, 180 mg of the antigen sought were obtained. The product contained from 34 to 36 bound steroid groups per mole of protein.

| Analysis: | UV Spectrum |
|---|---|
| in water: | max. at 265 nm $E_1^1$ = 79 |
|  | max. at 291 nm $E_1^1$ = 94 |
| in 0.1 N HCl | max. at 290 nm $E_1^1$ = 93 |

| | Circular dichroism |
|---|---|
| in water: | infl. towards 218 nm $\Delta E_1^1$ = −0.308 |
|  | max. at 259 nm $\Delta E_1^1$ = −0.115 |
|  | max. at 288 nm $\Delta E_1^1$ = +0.085 |
| in 0.1 N HCl | max. at 223 nm $\Delta E_1^1$ = −0.300 |
|  | max. at 283 nm $\Delta E_1^1$ = +0.037 |

Various modifications of the products and processes of the invention may be made without departing from the spirit or scope thereof and it is to be understood that the invention is intended to be limited only as defined in the appended claims.

What we claim is:

1. A radioactive estradiene labelled with iodine of the formula

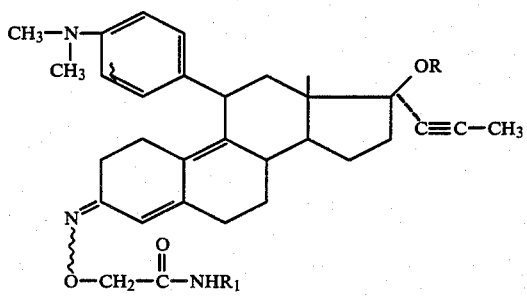

in the form of their sync or anti isomers or mixtures thereof wherein the wavy line indicates anti or syn position, R is selected from the group consisting of hydrogen, alkyl of 1 to 6 carbon atoms and acyl of an organic carboxylic acid of 1 to 12 carbon atoms and R$_1$ is the residue of an an amino acid R$_1$NH$_2$ possessing an iodine acceptor group or a derivative thereof labelled with iodine$^{125}$ or $^{131}$.

2. A compound of claim 1 wherein the amino acid is selected from the group consisting of histidine, tyrosine, histamine, tyramine and methyl tyrosinate, labelled with iodine$^{125}$ or $^{131}$.

3. A compound of claim 1 selected from the group consisting of 3-carboxymethyloxime of 11β-(4-dimethylaminophenyl)-17α-(prop-1-ynyl)-Δ⁴,⁹-estradiene-17β-ol-3-one, in the form of a mixture of syn isomer and anti isomer, in the form of the syn isomer and in the form of the anti isomer coupled to ($^{125}$I) histamine with the iodine being in the 2- or 5-position of the formula

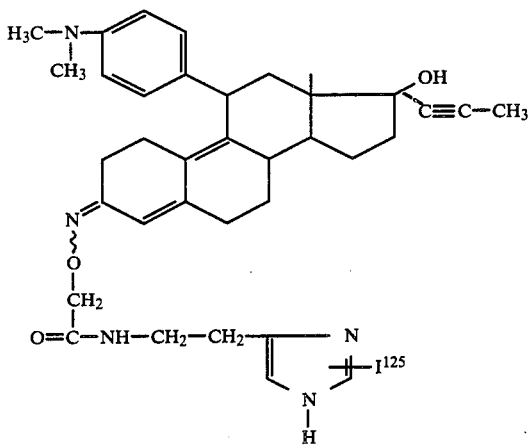

4. A process for the preparation of a compound of claim 1 comprising reacting a product of the formula

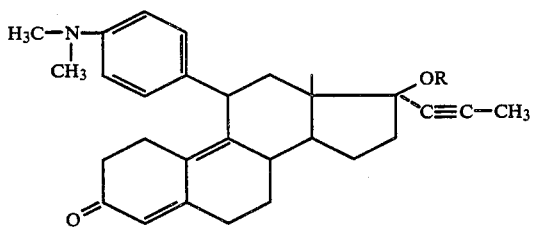

wherein R has the above definition with a carboxymethoxylamine halide in the presence of a base to obtain a compound of the formula

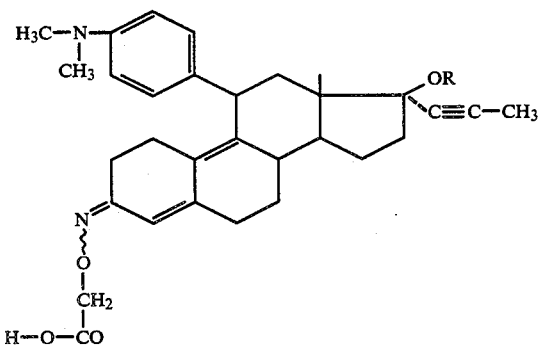

wherein the wavy line on the nitrogen indicates that the product is in the form of a mixture of syn and anti isomers, then reacting the latter with alkyl haloformate to obtain a compound of the formula

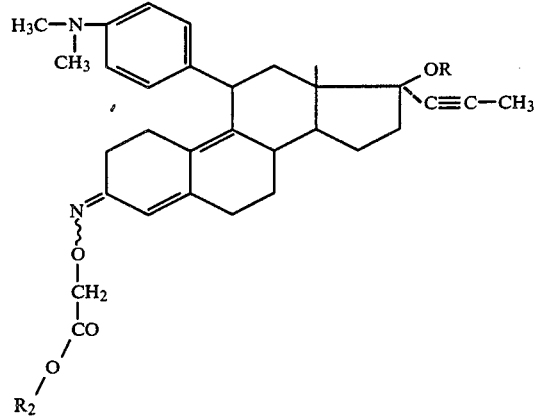

wherein $R_2$ is an activator group of the carbonyl function and the wavy line on the nitrogen indicates that this product is in the form of a mixture of syn and anti isomers and reacting the latter with an amino acid $R_1NH_2$ possessing an iodine acceptor group labelled with iodine$^{125}$ or $^{131}$ or with a derivative thereof to obtain the corresponding compound of claim 1, which is isolated in the form of a mixture of syn and anti isomers, or which is separated, if desired, into its isomers, then, if necessary the 17-hydroxy function is etherified or esterified.

5. The process of claim 4 wherein the iodine acceptor amino acid or the derivative of this amino acid is selected from the group consisting of histidine, tyrosine, histamine, tyramine and methyl tyrosinate.

6. The process of claim 4 wherein the carboxymethoxylamine halide is carboxymethoxylamine hemihydrochloride and the operation is carried out under an inert atmosphere and in the presence of sodium hydroxide; reacting alkyl haloformate in the presence of a tertiary base in an anhydrous medium and under an inert atmosphere.

7. The process of claim 6 wherein the alkyl haloformate is isobutyl chloroformate and the operation is carried out in the presence of tri-n-butylamine.

8. The process of claim 4 wherein the amino acid is histamine labelled with iodine$^{125}$ or $^{131}$ and the operation is carried out under an inert atmosphere.

9. The process of claim 4 wherein the starting material is 11β-(4-dimethylaminophenyl)-17α-(prop-1-ynyl)-Δ⁴,⁹-estradiene-17β-ol-3-one.

10. In the method for the study and radioimmunological determination of non-radioactive 11β-(4-dimethylaminophenyl)-17α-(prop-1-ynyl)-Δ⁴,⁹-estradiene-17β-ol-3-one in biological fluids of humans and warm-blooded animals, the improvement comprising using a compound of claim 1 for the study and determination.

11. The method of claim 10 wherein the compound used is a compound of claim 3.

12. A compound selected from the group consisting of anti isomer, syn isomer or mixtures thereof of a compound of the formula

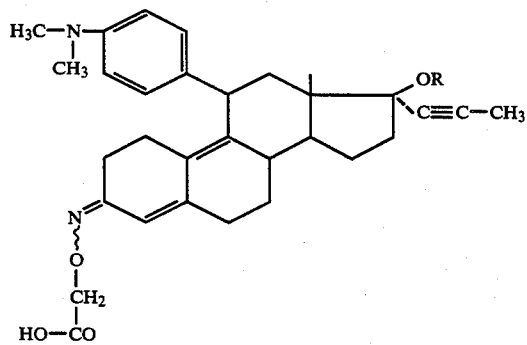

III

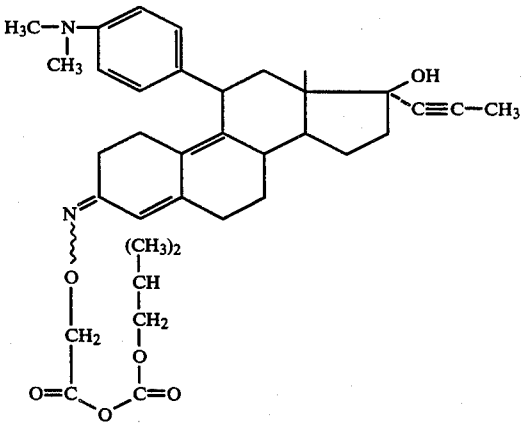

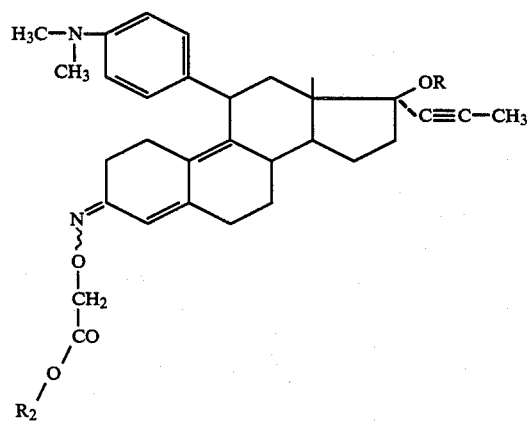

IV

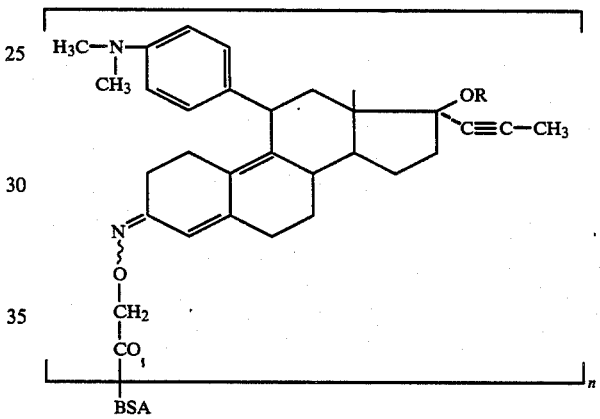

wherein the wavy line on the oximine nitrogen indicates that the oxime function can be in the syn or the anti position and R is selected from the group consisting of hydrogen, alkyl of 1 to 6 carbon atoms and acyl of an organic carboxylic acid of 1 to 12 carbon atoms and $R_2$ is an activator of the carbonyl function.

13. A compound of claim 12 selected from the group consisting of the 3-carboxymethyloxime of 11β-(4-dimethylaminophenyl)-17α-(prop-1-ynyl)-Δ$^{4,9}$-estradiene-17β-ol-3-one in the form of a mixture of syn and anti isomers, in the form of the syn isomer and in the form of the anti isomer the mixed anhydride of 3-carboxymethyloxime of 11β-(4-dimethylaminophenyl)-17α-(prop-1-ynyl)-Δ$^{4,9}$-estradiene-17β-ol-3-one with isobutyl formate in the form of a mixture of syn and anti isomers or in the form of the syn isomer and the anti isomer:

14. An antigen selected from the group consisting of antigens of the formulae

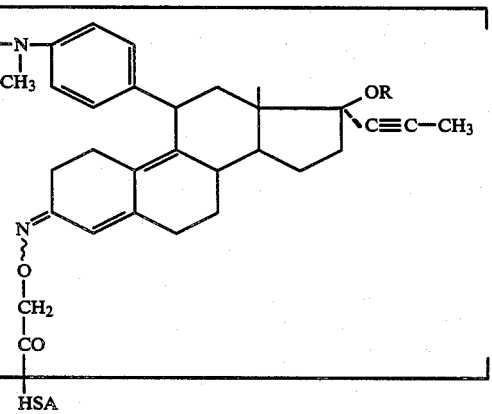

and

[structure with HSA]

wherein n is 20 to 30 and the oxime part of the steroid is in the form of the syn isomer, in the form of the anti isomer or in the form of a mixture of syn and anti isomers.

15. In the preparation of antibodies, the improvement comprising using as the antigen an antigen of claim 14.

* * * * *